United States Patent
Carroll

(10) Patent No.: US 8,628,507 B1
(45) Date of Patent: Jan. 14, 2014

(54) DISPOSABLE NURSING PAD

(75) Inventor: Teresa P. Carroll, Athens, AL (US)

(73) Assignee: NuAngel, Inc., Athens, AL (US)

( * ) Notice: Subject to any disclaimer, the term of this patent is extended or adjusted under 35 U.S.C. 154(b) by 349 days.

(21) Appl. No.: 12/779,765

(22) Filed: May 13, 2010

Related U.S. Application Data

(60) Provisional application No. 61/177,783, filed on May 13, 2009.

(51) Int. Cl.
*A61F 5/44* (2006.01)

(52) U.S. Cl.
USPC .......................................... 604/346; 604/358

(58) Field of Classification Search
USPC ............ 604/327, 346, 358; 2/104; 450/54–57
See application file for complete search history.

(56) References Cited

U.S. PATENT DOCUMENTS

| | | | |
|---|---|---|---|
| 2,891,544 A | | 6/1959 | London |
| 3,442,268 A | * | 5/1969 | Bird .............................. 604/380 |
| 4,047,534 A | * | 9/1977 | Thomaschefsky et al. ... 604/365 |
| 4,074,721 A | | 2/1978 | Smits et al. |
| 5,104,396 A | | 4/1992 | Oatley et al. |
| 5,149,336 A | | 9/1992 | Clarke et al. |
| 5,683,286 A | * | 11/1997 | Kielland ......................... 450/37 |
| 5,690,536 A | | 11/1997 | Madden et al. |
| 5,843,062 A | | 12/1998 | Reidmiller |
| H2062 H | | 4/2003 | Blaney et al. |
| 6,695,678 B1 | | 2/2004 | Foley et al. |
| 7,416,544 B2 | * | 8/2008 | Sakaguchi et al. ........ 604/385.07 |
| 2002/0022815 A1 | * | 2/2002 | Yamaji ............................. 450/37 |
| 2009/0209174 A1 | * | 8/2009 | Gonzales ........................ 450/57 |

FOREIGN PATENT DOCUMENTS

| | | |
|---|---|---|
| DE | 298 01 022 | 3/1998 |
| JP | 2008-297644 | 12/2008 |
| WO | 96/41601 | 12/1996 |
| WO | 01/43678 | 6/2001 |

* cited by examiner

*Primary Examiner* — Michele M Kidwell
(74) *Attorney, Agent, or Firm* — Angela Holt; Bradley Arant Boult Cummings LLP

(57) ABSTRACT

A disposable nursing pad is provided. The nursing pad of the present disclosure is thin, flexible, absorbent, breathable, hypoallergenic, and environmentally friendly. The pad of the present disclosure is composed of multiple layers—a cotton inner layer worn against the skin of the user, an absorbent middle layer, and a waterproof and breathable outer layer. The pad comprises a variety of embossed channels—one in the center of the pad, one along the perimeter of the pad, and radial channels extending from the perimeter channel towards the center channel.

18 Claims, 2 Drawing Sheets

(Section A-A)

DISPOSABLE NURSING PAD

CROSS-REFERENCE TO RELATED APPLICATIONS

This application claims the benefit of U.S. Provisional Application No. 61/177,783 filed on May 13, 2009, the entire contents of which are herein incorporated by reference.

FIELD OF THE INVENTION

The present invention relates generally to the maternity field. In particular, the present invention relates to a disposable nursing pad.

BACKGROUND AND SUMMARY OF THE INVENTION

The present invention consists of a disposable nursing pad. Nursing pads are worn against the skin and protect nursing mothers from dealing with embarrassing leakage on clothing. It is desirable to have a pad that is thin, flexible, absorbent, breathable, hypoallergenic, and environmentally friendly. The pad of the present disclosure provides each of these advantages, and is designed to be virtually invisible underneath the wearer's clothing. Some embodiments of the nursing pad are biodegradable. In others, the pad is chlorine and latex free. In one embodiment, the pad of the present disclosure is made of multiple layers. The pad can include a combination of a cotton layer, a biodegradable backing, and a middle layer composed of an airlaid material. Alternatively, the pad can include a combination of cotton, a biodegradable backing, and a spunlace layer.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

The disclosure can be better understood with reference to the following drawings. The elements of the drawings are not necessarily to scale, emphasis instead being placed upon clearly illustrating the principles of the disclosure. Furthermore, like reference numerals designate corresponding parts throughout the several views.

DETAILED DESCRIPTION

Figure 1:
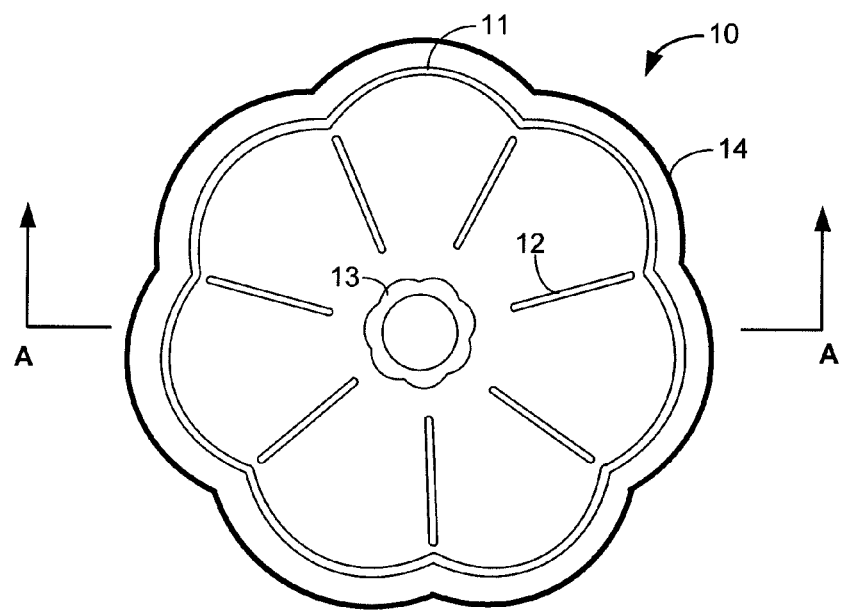
FIG. 1 is a front view of the nursing pad of the present disclosure.

FIG. 1 is a top view of a nursing pad 10 according to an embodiment of the present disclosure. In this embodiment, the pad 10 is somewhat circular in shape with a scalloped edge 14. A recessed perimeter channel 11 extends around the perimeter of the pad 10, and is useful for preventing pad edge separation, as well as to divert leakage off of the edge of the pad. A plurality of recessed radial channels 12 extend radially from near the center of the pad 10 out toward the perimeter channel 11. An inner ring channel 13 is recessed into the central area of the pad 13. The channels 11, 12, and 13 are formed by a hydraulic press (not shown) in an embossing process that imprints the channels into the pad.

The perimeter channel 11 diverts breast milk (not shown) to help minimize the risk of leakage around the outer edge 14 of the pad 10. The radial channels 12 and inner ring channel 13 helps the pad to contour to the shape of the wearer's breast. The radial channels 12 further help channel milk away from the center of the pad 10 and to distribute it throughout the pad to prevent leakage. The inner ring channel 13 assists the wearer in placing it properly on the wearer's body, namely over the wearer's nipple.

Figure 2:
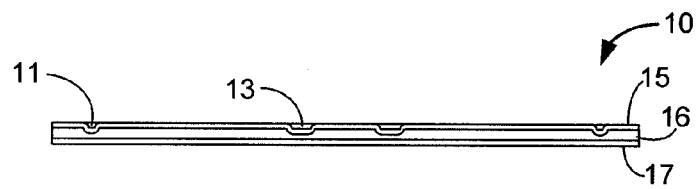
FIG. 2 is a side view of the nursing pad of FIG. 1 taken along section lines A-A.

FIG. 2 is a cross-sectional view of the pad 10 of FIG. 1, taken along section lines A-A of FIG. 1. In this embodiment, the pad 10 is comprised of an inner layer 15, a middle layer 16, and an outer layer 17. The inner layer 15 contacts the wearer's skin and is fabricated from 100% cotton in one embodiment. The middle layer 16 is comprised of "fluff" material, which is fabricated from pulp in one embodiment. In some embodiments, the middle layer 16 is comprised of absorbent material known in the art such as superabsorbent polymers. The outer layer 17 is fabricated from a disposable waterproof material known in the art. In some embodiments, the outer layer 17 is biodegradable.

Figure 3:
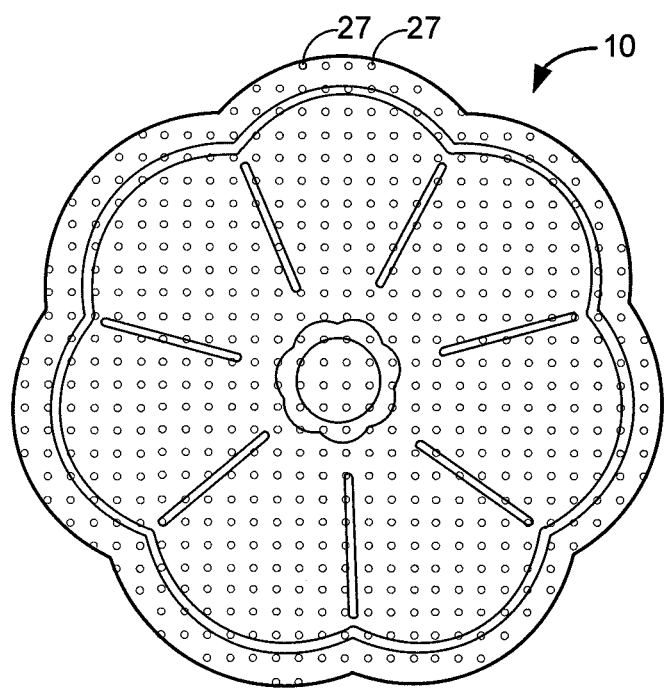
FIG. 3 is a front view of an alternative embodiment of the present disclosure.

FIG. 3 is an alternative embodiment. In the alternative embodiment, dimples 27 may be embossed on both sides of the pad 10 and function as additional "traps" for liquids. Furthermore, the embossed dimples 27 help hold the various layers of the pad 10 together, eliminating the need for glues or binders.

In order to manufacture the pad of the present invention, layers 15-17 are compressed together in the hydraulic press utilizing a pre-formed die (not shown) that forms the channels 11-13. In order to achieve the desired pattern, and to create the channels 11-13 of the desired depth, the pressure and temperature of the press may be adjusted. The channels 11, 12 and 13 are recessed into the pad 10 as discussed above. The embossing holds the layers 15-17 together without a need for glues or binders.

As described above and shown in the associated drawings, the present invention comprises an apparatus that adjustably attaches to a users forearm and contains various clips, holders, and attachment means for the inclusion of a variety of office supplies. While particular embodiments of the invention have been described, it will be understood, however, that the invention is not limited thereto, since modifications may be made by those skilled in the art, particularly in light of the foregoing teachings. It is, therefore, contemplated by the appended claims to cover any such modifications that incorporate those features or those improvements that embody the spirit and scope of the present invention.

What is claimed is:

1. A nursing pad comprising:
   a. a substantially circular base comprising scalloped edges;
   b. at least one embossed outer channel positioned along an outer edge of said base and extending around the perimeter to prevent leakage of breast milk; and
   c. at least one embossed inner channel positioned inwardly from the outer channel, where the inner channel a comprises a circle disposed on a central portion of the base,
   d. at least one radial channel positioned between said embossed perimeter channel and said embossed inner ring channel, said radial channel extending radially and linearly from near the center of the base outwardly toward the perimeter channel, said radial channel positioned to divert breast milk away from the center of the base.

2. The nursing pad of claim 1, wherein said base has a planar shape.

3. The nursing pad of claim 1, wherein said base is further comprised of an inner cotton layer, an absorbent middle layer, and a waterproof, breathable outer layer.

4. The nursing pad of claim 3, wherein said inner cotton layer is hypoallergenic.

5. The nursing pad of claim 1, wherein said base is biodegradable.

6. The nursing pad of claim 1 further comprising embossed dimples.

7. A nursing pad comprising:
 a. a substantially circular base;
 b. an embossed inner ring channel encircling a center portion of said base;
 c. an embossed perimeter channel along an outer edge of said base, the embossed perimeter channel positioned on a surface of said base to prevent leakage of breast milk, where a portion of said base is positioned between said perimeter channel and said outer edge of said base; and
 d. at least one radial channel positioned between said embossed perimeter channel and said embossed inner ring channel, said radial channel extending radially and linearly from near the center of the base outwardly to near the perimeter channel, each radial channel aligned with a radius of the base, said radial channel positioned to divert breast milk away from the center of the base.

8. The nursing pad of claim 7, wherein said base comprises scalloped edges.

9. The nursing pad of claim 7, wherein said base is further comprised of an inner cotton layer, an absorbent middle layer, and a waterproof breathable outer layer.

10. The nursing pad of claim 9, wherein said inner cotton layer is hypoallergenic.

11. The nursing pad of claim 9, wherein said inner cotton layer is biodegradable.

12. The nursing pad of claim 7 further comprising embossed dimples.

13. A nursing pad comprising:
 a. a substantially circular base;
 b. an embossed inner ring channel encircling a center portion of said base;
 c. an embossed perimeter channel positioned near an outer edge of said base to prevent leakage of breast milk, where a portion of said base is positioned between said perimeter channel and said outer edge of said base;
 d. a plurality of radial channels positioned between saw embossed perimeter channel and said embossed inner ring channel to divert breast milk away from the center portion of the base, each of the of radial channels extending in a substantially straight line outwardly and radially from near the center portion of the base to near the perimeter channel; and
 wherein said base has a planar shape.

14. The nursing pad of claim 13, wherein said outer edge of said base comprises scalloped edges.

15. The nursing pad of claim 14, wherein said base portion comprises an inner cotton layer, an absorbent middle layer, and a waterproof, breathable outer layer, wherein the inner cotton layer is hypoallergenic.

16. The nursing pad of claim 15, wherein said base is biodegradable.

17. The nursing pad of claim 16 further comprising embossed dimples.

18. The nursing pad of claim 1, wherein the embossed inner channel comprises a scalloped outer edge.

* * * * *